United States Patent [19]

Feldstein et al.

[11] Patent Number: 5,352,461
[45] Date of Patent: Oct. 4, 1994

[54] SELF ASSEMBLING DIKETOPIPERAZINE DRUG DELIVERY SYSTEM

[75] Inventors: Robert Feldstein, Pelham; John Glass, Shoreham; Solomon S. Steiner, Mt. Kisco, all of N.Y.

[73] Assignee: Pharmaceutical Discovery Corporation, Elmsford, N.Y.

[21] Appl. No.: 849,186

[22] Filed: Mar. 11, 1992

[51] Int. Cl.$^5$ ............................................. A61K 9/16
[52] U.S. Cl. .................................. 424/493; 424/489; 424/490
[58] Field of Search ............... 424/489, 490, 455, 493; 544/337, 231

[56] References Cited

U.S. PATENT DOCUMENTS

| | | | |
|---|---|---|---|
| 4,400,330 | 8/1983 | Wong et al. | 544/337 |
| 4,925,673 | 5/1990 | Steiner | 424/455 |
| 4,976,968 | 11/1990 | Steiner | 424/491 |
| 4,983,402 | 1/1991 | Steiner | 424/491 |

FOREIGN PATENT DOCUMENTS

| | | |
|---|---|---|
| 0216744 | 9/1986 | European Pat. Off. . |
| 0284039 | 9/1988 | European Pat. Off. . |
| 0333523 | 9/1989 | European Pat. Off. . |
| 0350246A2 | 1/1990 | European Pat. Off. . |
| 2145555 | 2/1973 | France . |
| WO91/06287 | 5/1991 | PCT Int'l Appl. . |
| 1155036 | 6/1969 | United Kingdom . |
| 1255805 | 12/1971 | United Kingdom . |

OTHER PUBLICATIONS

Katchalski, E., et al., "Synthesis of lysine anhydride," 68 J. Amer. Chem. Soc. 879–880 (1946).
Koppel, K. D., and H. G. Ghazarian, "A convenient synthesis of 2,5–diketopiperazinediones," 33 J. Organic Chem. 862–864 (1968).

Primary Examiner—Thurman K. Page
Assistant Examiner—W. Benston
Attorney, Agent, or Firm—Kilpatrick & Cody

[57] ABSTRACT

Drug delivery systems have been developed based on the formation of diketopiperazine (or analogs) microparticles. In the preferred embodiment the microparticle is stable at low pH and disintegrates at physiological pH, and is particularly useful for oral drug delivery. In the most preferred embodiment the microparticles are formed in the presence of the drug to be delivered, for example, insulin or heparin. The diketopiperazine synthetic intermediates are preferably formed by cyclodimerization to form diketopiperazine derivatives at elevated conditions under dehydrating conditions, then precipitated with drug to be incorporated into microparticles.

20 Claims, 3 Drawing Sheets

N-ε-Z-L-lysine cyclo-Lys(Z) - Lys(Z)

2,5-Diketo-3,6-di(4-aminobutyl) piperazine 2,5-Diketo-3,6-di(4-succinylaminobutyl) piperazine

SELF ASSEMBLING DIKETOPIPERAZINE DRUG DELIVERY SYSTEM

BACKGROUND OF THE INVENTION

This invention is generally in the area of drug delivery systems and is particularly related to reversible microencapsulation of drugs by certain 2,5-diketo-derivatives of piperazine.

Delivery of drugs has been a major problem for many years. It is particularly a problem when the compound to be delivered is unstable under the conditions encountered when administered to the patient, prior to reaching its targeted location. For example, it is preferable in many cases to administer drugs orally, especially in terms of ease of administration, patient compliance, and decreased cost. However, many compounds are ineffective or exhibit low or variable potency when administered orally. Presumably this is because the drugs are unstable to conditions in the digestive tract or because they are inefficiently absorbed.

The field of oral drug delivery covers a broad range of delivery systems ranging from simple mechanical carriers such as pressed tablets which transport compounds that can be safely and efficiently delivered through the stomach, to enteric coatings which delay the release of the encapsulated compound to later in the digestive process and lower in the gastrointestinal tract. A variety of enteric coatings have been used to encapsulate and protect the drug prior to reaching the small intestine. In some cases these are effective. However, there are drugs that are also unstable to the conditions present in the small intestine and therefore must be administered in much higher dosages if the drug is to be released in the small intestine for an effective amount to penetrate to the bloodstream. In these cases, it is necessary to have a mechanism whereby the coating is not only stable to the conditions present in the digestive tract, as well as to the conditions under which it is stored prior to administration to the patient, but which allows the encapsulated drug to pass into the bloodstream.

Other factors in drug delivery system design include the requirements that the system must be non-toxic, non-reactive with the drug to be delivered, not too expensive or difficult to manufacture, formed of readily available components, and consistent with respect to final composition and physical characteristics, including stability and release rate. The system must also be formed of materials that are easily removed by normal metabolic processes.

A number of different systems have been proposed, most based on peptides or biodegradable natural or synthetic polymers, such as the natural polysaccharides or polylactic acid, polyglycolic acid, polyorthoesters, or polyanhydrides, alone or within an appropriate enteric coating, for example, as described by EPA 0 333 523 by The UAB Research Foundation and Southern Research Institute. With the exception of this synthetic polymeric system and two protein-based systems, the proteinoid microspheres described in Steiner and Rosen U.S. Pat. Nos. 4,925,673, 4,983,402, and 4,976,968 and the zein microspheres described in PCT application WO 91/06287 by Enzytech, none of these systems is stable to conditions in the stomach. Only the proteinoid system is designed particularly to be stable to the lower pH of the stomach and unstable to the higher pH of the blood.

The most desirable delivery system from a manufacturing standpoint is one that is self assembling from simple, chemically defined precursors, which are stable over the pH, temperature and solvent range of interest, yet resistant to rapid protease attack. Ideally, these precursors are economical and available, using available technology, in production volume.

One of the best known self-assembling encapsulation systems is the amino acid polymer self-assembling microcapsules first pioneered by Dr. Sidney Fox (Molecular Evolution and the Origin of Life). The initial experiments were with "proteinoids", a "linear thermal condensation polymer of a mixture of naturally occurring amino acids", the same system subsequently patented by Steiner and Rosen for drug delivery. While this did in fact demonstrate a capacity for self-organization under conditions plausible for early evolution, the behavior of the system is undesirable as an encapsulation technology. The stochastic nature of the precursors and the further stochastic nature of self assembly of linear polymers are inappropriate for a controllable process.

Accordingly, there remains a significant economic and medical need for an effective method for the oral delivery and release of therapeutic agents which are poorly absorbed by or unstable in the gastrointestinal tract.

It is therefore an object of the present invention to provide a system for drug delivery.

It is a further object of the present invention to provide a system which, by intentional modifications to its structure, can be made to be stable or unstable in a variety of physiological conditions.

It is another object of the present invention to provide a system which is self-assembling and can be manufactured economically from currently available reagents.

SUMMARY OF THE INVENTION

Drug delivery systems have been developed based on the formation of diketopiperazine microparticles. In the preferred embodiment the microparticle is stable at low pH and disintegrates at a pH of about 6.5 or greater, and is particularly useful for oral drug delivery. In the most preferred embodiment the microparticles are formed in the presence of the drug to be delivered, for example, insulin or heparin. The diketopiperazine microparticles are preferably formed in the presence of the drug to be encapsulated by acidification of weakly alkaline solutions of a diketopiperazine derivative that contains one or more carboxylic acid groups.

Examples demonstrate that encapsulation and administration of insulin in rats results in subsequent control of blood glucose. Encapsulation of heparin also results in controlled release of heparin under physiological conditions and inhibits blood coagulation.

DETAILED DESCRIPTION OF THE INVENTION

Figure 1:
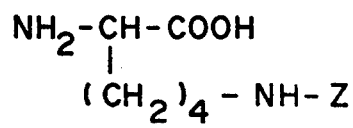
FIG. 1 is a schematic of the synthesis of 2,5-diketo-3,6-di(4-succinylaminobutyl)piperazine.
Figure 1:
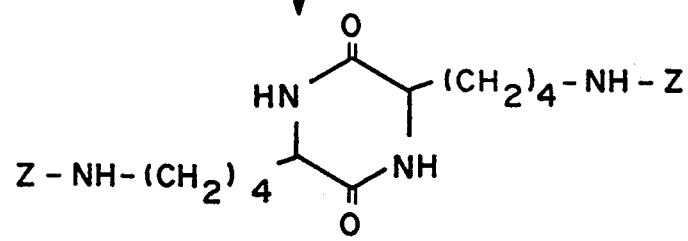
Figure 1:
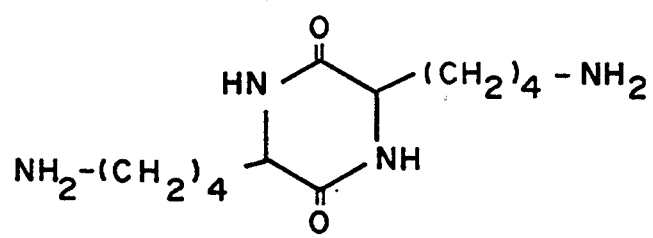
Figure 1:
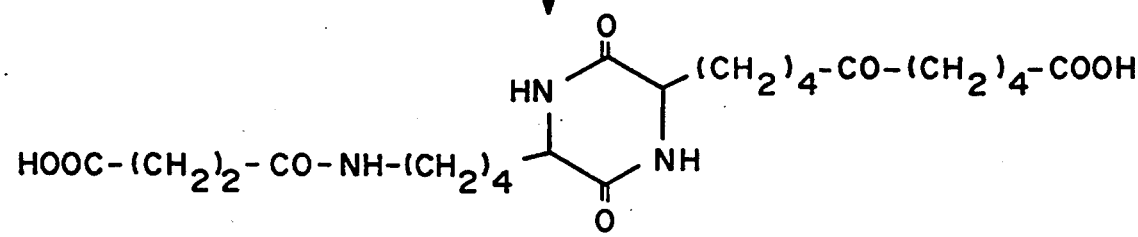

The present invention is a drug delivery system using diketopiperazines to form microparticles encapsulating a drug to be delivered.

As used herein, the term "microparticles" includes microcapsules having an outer shell surrounding a core material; microspheres containing drug dispersed throughout the sphere; and microparticles of irregular shape. In the preferred embodiment, the microparticles are microspheres of between 0.1 to ten microns in diameter.

As used herein, "drug" and "cargo" refer to the pharmacologically active agent incorporated into the microparticles.

A clinically viable micro-encapsulation system should ideally be constructed from a chemically-defined synthetic subunit. The subunit should be of minimum complexity to permit toxicity and efficacy data to be derived to establish both safety and reproducible bioavailability with an acceptably narrow range of deviation from lot to lot (manufacturability).

The system should be self-assembling under closely controllable conditions, which conditions are benign to a range of potential drugs to be encapsulated. While the charge distribution, solubility and hydrophobicity of the cargo must clearly have some influence on assembly, a well-selected system should accept, with little modification, a range of drug cargoes. For specific cargoes, the material can optimized with minor structural manipulations.

The basic building blocks of a self-assembling system should be nonlinear in structure and should be synthesized to provide a known non-stochastic starting structure. Furthermore, the pH-dependent assembly/disassembly range should be closely controlled and defined.

There are a wide variety of sufficiently rigid structures which could constitute useful and stable self-assembling systems. Such rigid structures include amino acids and other components. The use of planar rings provides excellent stiffness, reducing the degree of freedom and therefore the variability in performance. The nucleic acids adenine and guanine are examples of the type of structures displaying significant stiffness, comprising six member rings that share an edge with five member rings. This rigidity and stability may account for their evolutionary selection as genetic code elements, imparting dimensional stability in bridging the double helix. Similarly, the use of an "end cap" on a polymer such as pyroglutamate (a pentagonal bonding agent) increases the stability of the system by aiding in "surface tiling" to provide a net curvature to a cross-linked sheet.

A preferred planar ring element that provides excellent rigidity and appropriate attachment sites for synthetic variation is diketopiperazine or one of its substitution derivatives, including diketomorpholines, diketodioxanes or others. A system based upon diketopiperazine structural elements forms microparticles with desirable size distributions and pH ranges as well as good cargo tolerance. A wide range of stable, reproducible characteristics can be generated with appropriate manipulations of the attachment sites, resulting in substantial yields and excellent reproducibility.

The direct synthesis of the precursors reduces the variability in bioavailability that plagued previous systems and, perhaps more important, removes the threat of an unpredictable toxic event. Toxicity, size, pH range and cargo capacity should be stable, experimentally verifiable parameters of the system.

Diketopiperazines

The diketopiperazines or their substitution analogs are rigid planar hexagonal rings with opposing heteroatoms and unbonded electron pairs. One or both of the nitrogens can be replaced with oxygen to create the substitution analogs diketomorpholine and diketodioxane, respectively. Although it is possible to replace a nitrogen with a sulfur atom, this does not yield a stable structure. The general formula for diketopiperazine and its analogs is shown below.

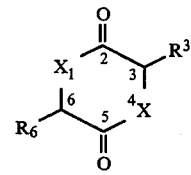

wherein the ring atoms X at positions 1 and 4 are either O or N; and at least one of the side-chain substituents R at positions 3 and 6 contains an ionizable group such as a carboxyl group if the composition is used for oral delivery and exhibits pH-dependent assembly-disassembly, one or both must be ionizable to control release conditions. As used herein, "diketopiperazines" includes diketopiperazines and derivatives and modifications thereof falling within the scope of the above-general formula.

An example of a preferred compound, 2,5-diketo-3,6-di(4-succinylaminobutyl)piperazine, wherein X is N, and $R_3$ and $R_4$ are $(CH2)_4-NH-CO-(CH2)_2-COOH$, is shown below:

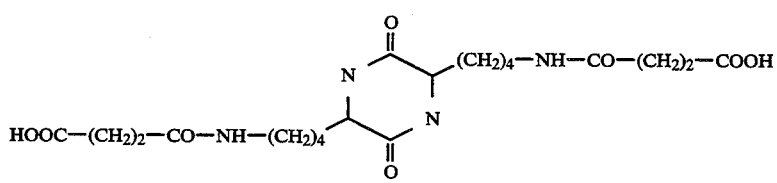

Methods for Synthesis of the Diketopiperazines

Diketopiperazines can be formed by cyclodimerization of amino acid ester derivatives, as described by Katchalski, et al., *J. Amer. Chem. Soc.* 68, 879–880 (1946), by cyclization of dipeptide ester derivatives, or by thermal dehydration of amino acid derivatives in high-boiling solvents, as described by Kopple, et al., *J. Org. Chem.* 33(2), 862–864 (1968), the teachings of which are incorporated herein. 2,5-diketo-3,6-di(aminobutyl)piperazine (Katchalski et al. refer to this as lysine anhydride) was conveniently prepared via cyclodimerization of N-epsilon-Z-L-lysine in molten phenol, similar to the Kopple method in *J. Org. Chem.*, followed by removal of the blocking (Z)-groups with 4.3M HBr in acetic acid. This route is preferred because it uses a commercially available starting material, it involves reaction conditions that are reported to preserve stereochemistry of the starting materials in the product and all steps can be easily scaled up for manufacture.

The synthesis of 2,5-diketo-3,6-di(4-succinylaminobutyl)piperazine is shown schematically in FIG. 1. 2,5-diketo-3,6-di(aminobutyl)piperazine is exhaustively succinylated with succinic anhydride in mildly alkaline aqueous solution to yield a product which is readily soluble in weakly alkaline aqueous solution, but which is quite insoluble in acidic aqueous solutions. When concentrated solutions of the compound in weakly alkaline media are rapidly acidified under appropriate conditions, the material separates from the solution as microparticles.

The succinylated compound, 2,5-diketo-3,6-di(4-succinylaminobutyl)piperazine, where $R_3$ and $R_4$ are $(CH_2)_4$—NH—CO$(CH_2)_2$—COOH, is shown above.

Methods for forming microparticles and encapsulating drug

In the preferred embodiment, drug is encapsulated within microparticles by dissolving the diketopiperazine in bicarbonate or other basic solution, adding the drug in solution or suspension to be encapsulated, then solidifying the structure by adding acid, such as 1M citric acid.

The microparticles can be stored in the dried state and reconstituted for administration to a patient. In the preferred embodiment, the reconstituted microparticles maintain their stability in an acidic medium and open up as the medium approaches physiological pH in the range of 6.5. However, materials, such as cyclo-Lys(Z)-Lys(Z) synthetic intermediate treated with a limiting amount of HBr in acetic acid to remove one rather than both of the Z groups, are soluble in weakly acidic aqueous solutions and precipitate when the solution is made weakly alkaline with sodium bicarbonate, and could be used to form microparticles for drug delivery where it is desirable to achieve release under acidic conditions, for example, following phagocytosis and endocytosis into lysosomes. Another material that should exhibit this response to pH was obtained by heating diketopiperazine with succinic anhydride in refluxing toluene, which is expected to yield a diketopiperazine derivative N-succinylated at the 1 and 4 positions of the ring.

Materials that can be encapsulated

For drug delivery, biologically active agents having therapeutic, prophylactic or diagnostic activities can be delivered. These can be organic or inorganic compounds, proteins, or a wide variety of other compounds, including nutritional agents such as vitamins, minerals, amino acids and fats. In the preferred embodiments, the materials are biologically active agents that are to be released in the circulatory system after transport from the GI tract following oral delivery. Examples include proteins and peptides (wherein protein is defined as consisting of 100 amino acid residues or more and a peptide is less than 100 amino acid residues), such as insulin and other hormones, polysaccharides, such as heparin, nucleic acids (such as antisense), lipids and lipopolysaccharides, and organic molecules having biological activity such as many of the antibiotics, anti-inflammatories, antivitals, vaso- and neuroactive agents. Specific examples include hormones, anticoagulants, immunomodulating agents, cytotoxic agents, antibiotics, antivirals, antisense, antigens, and antibodies. In some instances, the proteins may be antibodies or antigens which otherwise would have to be administered by injection to elicit an appropriate response.

In the preferred embodiment, these biological agents are unstable in gastric acid, diffuse slowly through gastrointestinal membranes, and/or are susceptible to enzymatic destruction in the gastrointestinal tract. The biological agents are encapsulated to protect them in the gastrointestinal tract prior to release in the blood stream. In the preferred embodiments, the protective material, the diketopiperazines, are not biologically active and do not alter the pharmacologic properties of the therapeutic agents.

The microparticles are acid stable and hence resist the acidic environment of the stomach. In addition they are resistant to enzymatic degradation in the stomach. They are believed to pass through the endothelium into the blood stream where they become soluble in the near neutral pH of the blood, liberating the pharmacologically active compound.

Examples of agents include hormones, antigens, antibiotics, steroids, decongestants, neuroactive agents, and anesthetics or sedatives. The agents can be in various forms, such as uncharged molecules or components of molecular complexes. For acidic drugs, salts of metals, amines or organic cations (e.g., quaternary ammonium) can in some cases be used. Simple derivatives of the drugs (such as ethers, esters, and amides), which have desirable retention and release characteristics, can also be used. It is not possible to have independent control of salt forms of the drug if acids and bases are being used to control the formation of the microparticles. It is not possible to have a drug molecule in the free-base or hydrochloride salt forms if the microparticles are formed by dissolving the diketopiperazine in sodium bicarbonate solutions and adding concentrated citric acid.

Imaging agents including metals, radioactive isotopes, radiopaque agents, and radiolucent agents, can also be incorporated. Radioisotopes and radiopaque agents include gallium, technetium, indium, strontium, iodine, barium, and phosphorus.

Pharmaceutical Compositions

The microparticles can be administered in suspension or encapsulated in another material such as an enteric coating or stabilizing agent such as albumin or lactose. These materials and methods for use thereof are well known to those in the pharmaceutical industry. The pharmaceutical composition may consist only of the microparticles or may further include the encapsulated compound, or other compounds. For example, it may be desirable to administer a compound that is stable to passage through the stomach that is then rapidly absorbed in one dosage in the intestine, followed by the more controlled, delayed release of the same or a different compound from the microparticles, i.e., enterically protected basic stable, neutral, soluble microcapsules, if the compound can tolerate encapsulation.

The microparticles can be administered topically, locally or systemically by parenteral administration or enteral administration.

Enteral Administration

Microparticles having biologically active agents are preferably administered orally. These microparticles, depending on the chemical nature and size, will either be absorbed to, or passed through, the epithelial lining of the gastrointestinal tract into the bloodstream or lymphatic system.

Parenteral Administration

Microparticles of less than five microns readily pass through a needle for intravenous administration. Suitable pharmaceutical carriers, for example, a phosphate buffered saline, are known and commercially available. Intravenous administration may be preferred for targeted delivery of incorporated compounds to phagocytic cells, for example, of antiparasitic or anti-HIV drugs, where the pathogenic agent is also selective for these cell types. Microcapsules should be stable at neutral pH and dissolve at low pH, the reverse of the oral system.

Subcutaneous, Intramuscular and Intraperitoneal Administration

Microparticles produced as described above are small enough to be injected through a standard gauge needle under the skin or into the peritoneum for subsequent release of incorporated drug. Adhesion of the microparticles to the peritoneum aids in localizing release of the incorporated drug. Microparticles can also be implanted or injected intramuscularly for immunization or other purposes where slower release into the bloodstream is desirable. Carriers such as phosphate buffer saline, or an adjuvant such as an oil, can be used as a carrier for the microparticles. Pharmaceutically acceptable carriers are known to those skilled in the art.

Topical Administration

Microparticles are suspended in a suitable pharmaceutical carrier for administration using methods appropriate for the carrier and site of administration. For example, microparticles are administered to the eye in a buffered saline solution, approximately pH 7.4, or in an ointment such as mineral oil. The dosage will be dependent on the compound to be released as well as the rate of release. The microparticles, or aggregations of microparticles into films, disks, or tablets, with incorporated compound can be administered to the skin in an ointment or cream. Suitable pharmaceutical carriers are known to those skilled in the art and commercially available.

Sustained delivery of antibiotics or growth factors (amino acids, peptides, or protein growth factors) to open wounds is of particular therapeutic importance in a variety of medical and surgical situations including, but not limited to, thermal burns, chemical burns, surgical wounds, diabetic ulcers and vascular insufficiency.

Diagnostic Applications

The microparticles containing radiopaque compounds, radioisotopes, or radiolucent compounds are particularly suited for use in diagnostic procedures. The microparticles can be administered parenterally or enterally. Microparticles that bind to mucosal membranes are particularly preferred for these applications, especially for imaging of the nasal and pharyngeal, gastrointestinal, and genito-urinary tracts. Intravenous administration of microparticles containing imaging agents are particularly useful for imaging liver, spleen or lung.

Targeted Administration

Delivery to specific cells, especially phagocytic cells and organs

Phagocytic cells within the Peyer's patches appear to selectively take up microparticles administered orally. Phagocytic cells of the reticuloendothelial system also take up microparticles when administered intravenously. Microparticles of less than five microns diameter can be injected without embolytic complications. Endocytosis of the microparticles by macrophages can be used to target the microparticles to the spleen, bone marrow, liver and lymph nodes.

The charge or lipophilicity of the microparticle is used to change the properties of the protein carrier. For example, the lipophilicity of the inner surface of the microcapsules can be modified by linking lipophilic groups to increase solubility of some drugs, thereby increasing drug cargo capacity. Other modifications can be made before or after formation of the microparticle, as long as the modification after formation does not have a detrimental effect on the incorporated compound.

Administration of the Microparticles to a Patient

In the preferred embodiment, the microparticles are stored lyophilized or encapsulated in standard gel capsule materials, for subsequent oral administration. The dosage is determined by the amount of encapsulated drug, the rate of release within the gastrointestinal tract, and the pharmokinetics of the compound.

In some embodiments, the microparticles can also be administered by injection, either intravenous, intramuscular, or subcutaneous, topically, or by means of a transdermal patch where release is activated by contact with the low pH of the skin (reverse stability formulation).

The present invention will be further understood by reference to the following non-limiting examples of the preparation and administration of diketopiperazine microparticles containing insulin.

EXAMPLE 1

Preparation of diketopiperazine microparticles cyclo-Lys(Z)-Lys(Z)

(Cyclodimerization of N-epsilon-(Z)-L-lysine)

The method of synthesis is shown schematically in FIG. 1.

The methods of Ephraim Katchalski, Issac Grossfeld, and Max Frankel, "Synthesis of lysine anhydride" *Journal of the American Chemical Society* 68, 879–880 (1946) and Kenneth D. Kopple and Hayop G. Ghazarian, "A convenient synthesis of 2,5-diketopiperazines" *Journal of Organic Chemistry* 33, 862–864 (1968) were adapted to use as follows. Katchalski et al describe the synthesis of the target compound by a different synthetic route; Kopple, et al describe a synthetic method similar to that used herein, but not using a lysine-based dipeptide nor yielding the same target compound. The letter "Z" is used to designate the benzyloxycarbonyl or carbobenzoxy group used to protect the amino group.

N-epsilon-Z-L-lysine

N-epsilon-Z-L-lysine (Sigma Chemical Co, St. Louis, Mo., 50 grams) was cyclized as follows. The compound was placed with 250 grams of crystalline phenol in a 500 mL resin reaction kettle under a gentle flow of nitrogen gas (prepurified grade). The temperature of the reaction mixture was raised to 175° C. (heating mantle) and held at that temperature under nitrogen for 18 hours. The reaction kettle was removed from the heating mantle and allowed to cool until the outside of the vessel was not warm to the touch and crystals were just beginning to form in the reaction mixture. The reaction mixture was then mixed with 1.5L anhydrous ether with stirring to precipitate a fine, white powder. This precipitate was collected on a sintered glass funnel (coarse grit) and washed on the filter with anhydrous ether. After air drying on the filter, the product (JG47) weighed 33.7 grams. A portion of the product (5 grams) was separated for analysis.

cyclo-Lys(Z)-lys(z)

The material was dissolved in 50 mL of hot glacial acetic acid and the solution was filtered to remove a small amount of insoluble material. On cooling, a solid crystallized from the acetic acid solution. This material was collected by filtration, then suspended in 200 mL 1:1 water:methanol. The suspension was brought to gentle reflux, then allowed to stand at room temperature for 2 days. The purified product (JG48) was collected by filtration and air dried on the filter. This procedure yielded 3.7 grams of purified cyclo-Lys(Z)-lys(z).

2,5-diketo-3,6-di(4-succinylaminobutyl)piperazine Dihydrobromide (Deprotection of cyclo-Lys(Z)Lys(Z))

To deprotect and leave terminal amino groups on the side chains, twenty grams of Cyclo-Lys(Z)-Lys(z) (JG47, finely powdered) was suspended in 50 mL of glacial acetic acid, with stirring. To this suspension was added 50 mL of 4.3M HBr in glacial acetic acid to remove the Z-group. For a time there was a rapid evolution of gas (carbon dioxide) and the solid dissolved almost completely; then a solid product began to separate from the reaction mixture.

Two hours after addition of the HBr solution, 150 mL of anhydrous ether was added to the mixture to complete precipitation of the product. The precipitated product was washed repeatedly with ether, then dried under a stream of dry nitrogen. The crystalline residue was used directly for succinylation.

2,5-diketo-3,6-di(4-aminobutyl)piperazine

The cyclo-Lys-Lys dihydrobromide from the preceding procedure was acylated into 2,5-diketo-3,6-di(4-aminobutyl)piperazine with succinic anhydride. First, it was dissolved in 200 mL of solution made by saturating water with sodium bicarbonate at room temperature. This dissolution was done slowly so that carbon dioxide gas could escape without causing the mixture to foam out of the reaction vessel. The solution was filtered to remove a small amount of insoluble material and the filter was washed with an additional 50 mL of saturated sodium bicarbonate solution which was added to the filtrate.

The solution was stirred with an efficient magnetic stirrer and with continuous monitoring of the pH using a glass electrode. The initial pH was 8.7. Succinic anhydride (30 grams) was added in ten portions. Each time the pH of the reaction mixture fell to 7.5, it was readjusted to 8.7 with 4M NaOH. The pattern of adding succinic anhydride and readjusting the pH was continued until all of the succinic anhydride was dissolved and the final pH stabilized (about half an hour after addition of the last portion of succinic anhydride).

To precipitate the microparticles, citric acid (10 grams) was added to the reaction mixture, then the pH was slowly adjusted to 2.2 with concentrated HCl. (There is a vigorous evolution of carbon dioxide during this process, which is controlled by slow addition of the HCl). At about pH 3-3.5, a solid product began to separate from the solution. At pH 2.2 the solution was filled with fine particles. The mixture was placed in the refrigerator overnight, then the product was collected by filtration, washed with water, and air dried on the filter. The yield was 11.7 grams of off-white powder (JG52).

A small sample of the product was dissolved in the minimum volume of water at the boiling point. The solid that separated on cooling was collected by centrifugation, washed with water, then lyophilized from a centrifugal pellet (JG77).

EXAMPLE 2

Suppression of Blood Glucose by Oral Administration of Insulin

Method

Porcine insulin (Signal Chemical Co., St. Louis, Mo., specific activity of approximately 26 U/mg) was encapsulated in 2,5-diketo-3,6-di(4-succinylaminobutyl)piperazine by dissolving the piperazine in a saturated sodium bicarbonate solution to form a 125 mg piperazine/mL solution, then mixing this solution with an equal volume of a 1M citric acid solution containing the insulin to be incorporated in a concentration of 20 mg insulin/ml. This yields a suspension of approximately 67.5 mg microparticles/ml.

In total, nine (9) male rats, each weighing approximately 250 g and having a normal blood glucose level, received by oral garage encapsulated insulin administered at a calculated dosage of between 1.25 and 2.0 mg insulin/kg of body weight. For controls, rats received an amorphous precipitate of the polymer and insulin prepared so that no insulin was encapsulated in spheres, but the concentration of insulin in the final solution was the same as that used in the original preparation. When this suspension was administered by oral gavage to four control rats, at a dose of 1 ml of suspension/kg of body weight, no significant decrease in blood glucose was noted. Additionally, subjects were administered insulin subcutaneously as both an aqueous solution and in the form of an amorphous precipitate to demonstrate the biological activity of the insulin itself.

Blood glucose levels were measured on samples taken from the tail at various times after treatment and measured as mg of glucose/dl of blood using one drop of tail blood squeezed onto a Glucofilm strip.

Figure 2A:
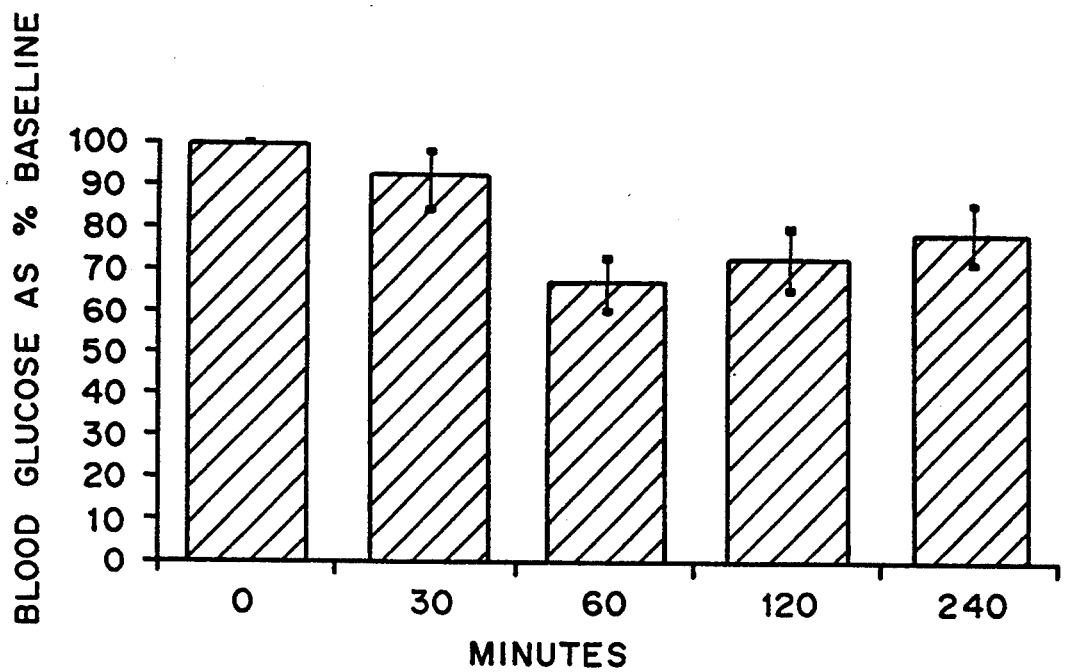
FIG. 2a is a graph of the average percent reduction in blood glucose levels measured in mg/dl for four and five subjects, respectively, receiving 1 ml of encapsulated insulin/kg of body weight at various time intervals (hours).
Figure 2B:
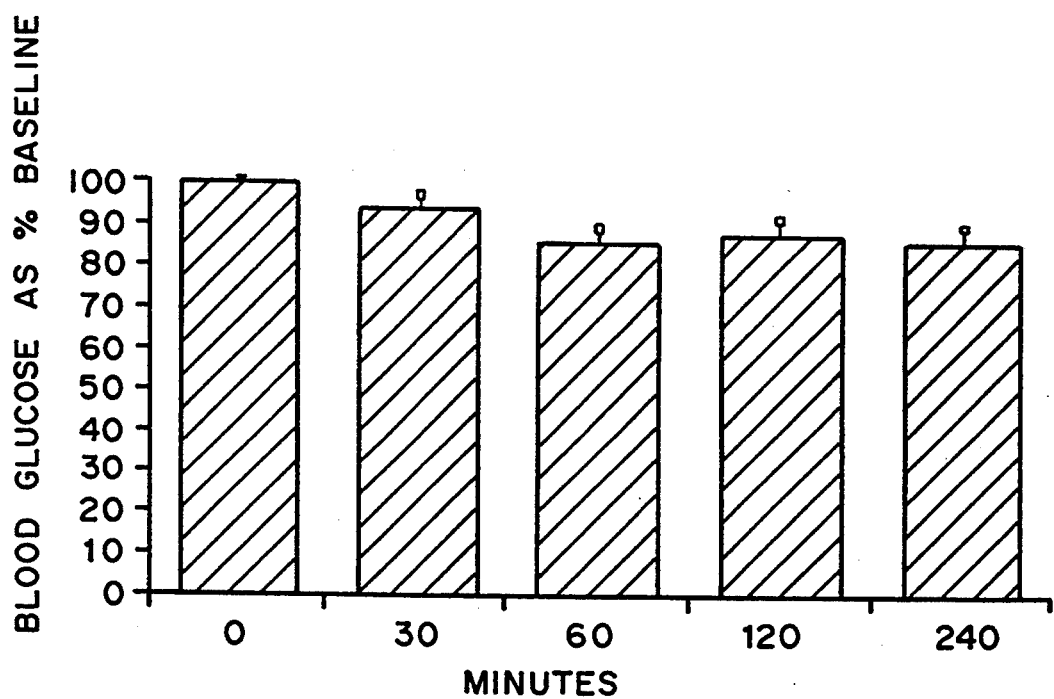
FIGS. 2b is a graph of the average percent reduction in blood glucose measured in mg/dl over time (hours), following administration of the microparticles not containing insulin.

Results: FIG. 2a presents the average percent reduction in blood glucose levels measured in (mg/dl) for nine subjects receiving 1 ml of encapsulated insulin suspension at a concentration of 10 mg/kg of body weight at various time intervals. The encapsulated insulin produced a marked fall in blood glucose levels when administered orally. Oral administration of an amorphous precipitate solution of the polymer with the same amount of insulin failed to produce a significant change in blood glucose levels, as shown by FIG. 2b. The same solution injected subcutaneously produced a characteristic drop in blood glucose; as did an injection of pure insulin in an aqueous solution. The absence of a pharmacologic effect with oral administration of unencapsulated insulin is consistent with the findings of other studies in the literature done at higher doses in both animals and humans. FIG. 2a demonstrates that blood glucose levels are returning to preadministration values at 240 minutes.

EXAMPLE 3

Inhibition of Clotting in Blood by Microencapsulated Heparin

Heparin (Sigma Chemical Co., St. Louis, Mo., specific activity approximately 26 U/mg)) was encapsulated as described above by dissolving the disuccinyl derivative of 2,5-deketo-3,6-di(4-aminobutyl)piperazine in a saturated sodium bicarbonate solution to a concentration of 120 mg piperazine/mL of solution, then mixing this with an equal volume of 1M citric acid containing 100 mg sodium heparin/mL citric acid.

The final suspension contained 50 mg of heparin/ml of suspension. Of this, approximately 20% was encapsulated, yielding a theoretical maximum concentration of encapsulated heparin of 10 mg of heparin per ml of suspension.

The solution containing encapsulated heparin was administered to eight rats weighing approximately 250 grams, by oral garage. The rats were fasted overnight prior to treatment. Each rat received 1 ml of suspension per kg of body weight. Additionally, a suspension of microcapsules formed in 1 M citric acid with no heparin present was administered to a group of four (4) control rats.

Figure 3A:
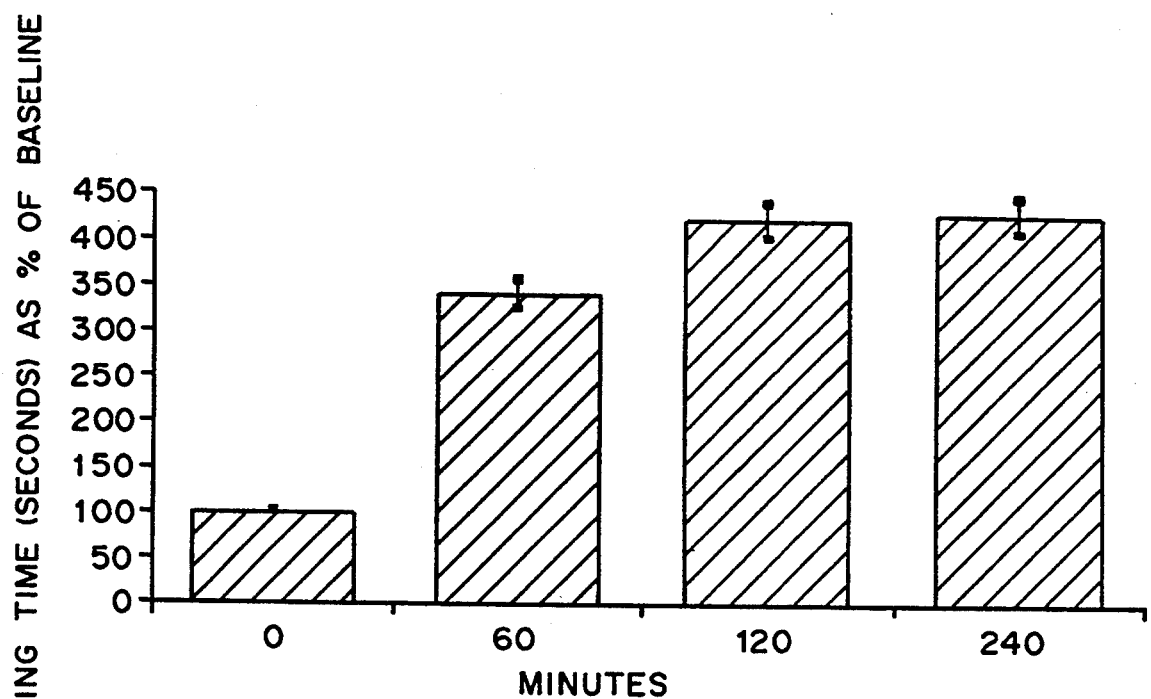
FIG. 3a is a graph of the clotting time (seconds) as % of baseline over time (minutes) for plasma from animals which have received encapsulated heparin by oral garage.

At zero minutes, 60 minutes, 120 minutes, 240 minutes, and 360 minutes, blood was drawn into a citrated syringe in a ratio of 9:1. The blood was immediately centrifuged and the plasma assayed using the APTT assay with standard reagents. The results are shown in FIG. 3a. The results clearly indicate that the oral administration of heparin was effective in prolonging clotting times.

Figure 3B:
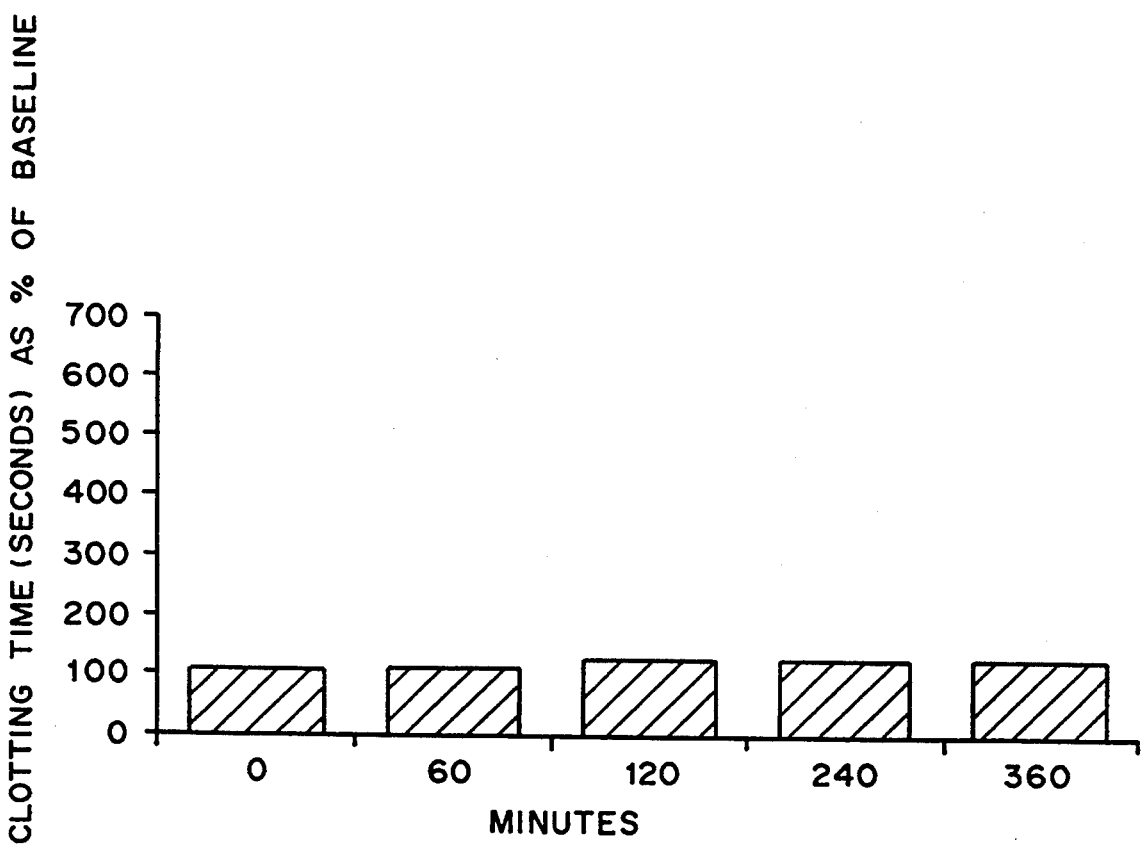
FIG. 3b is a graph of the clotting time (seconds) as % of baseline over time (minutes) for plasma from animals which have received microparticles not containing heparin by oral garage.

FIG. 3b shows the results of the control group. The results clearly indicate that the microparticles themselves do not appreciably effect clotting time.

Modifications and variations of the method of the present invention will be obvious to those skilled in the art from the foregoing detailed description. Such modifications and variations are intended to come within the scope of the appended claims.

We claim:

1. A microparticulate system for drug delivery comprising:
   diketopiperazine microparticles incorporating a biologically active agent selected from the group consisting of proteins, peptides, polysaccharides, lipids, lipopolysaccharides, nucleic acids and other biologically active organic molecules,
   wherein the microparticles are stable at a first defined pH due to association and precipitation of the diketopiperazines and unstable at a second defined pH due to dissociation of the diketopiperazines.

2. The system of claim 1 wherein the diketopiperazine has the general structure

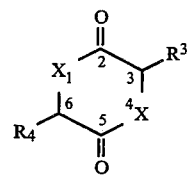

wherein the ring atoms X at positions 1 and 4 are either O or N; and
at least one of the side-chain substituents R at positions 3 and 6 contains a carboxyl group.

3. The system of claim 2 wherein the structure is formed from amino acids selected from the group consisting of glutamic acid, aspartic acid, lysine, ornithine and diaminopropionic acid.

4. The system of claim 3 wherein the structure is selected from the group consisting of 2,5-diketo-3,6-di(aminobutyl)piperazine and 2,5-diketo-3,6-di(4-succinylaminobutyl)piperazine.

5. The system of claim 1 wherein the microparticles are stable at acidic pH and unstable at a more basic pH.

6. The system of claim 1 wherein the microparticles are unstable at acidic pH and stable at a more basic pH.

7. The system of claim 1 wherein the biological agent is insulin.

8. The system of claim 1 wherein the biological agent is heparin.

9. A method for making a microparticulate system for drug delivery comprising
   forming diketopiperazines in a solution with a first defined pH at which the diketopiperazines are soluble,
   adding to the diketopiperazine solution a biologically active agent selected from the group consisting of proteins, peptides, polysaccharides, lipids, lipopolysaccharides, nucleic acids and other biologically active organic molecules, imaging agents, and cell specific targeting agents, in a solution having a second defined pH precipitating the diketopiperazines to form microparticles of the diketopiperazines containing the biologically active agent.

10. The method of claim 9 wherein the diketopiperazine has the general structure

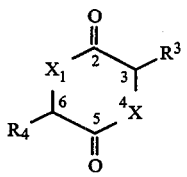

wherein the ring atoms X at positions 1 and 4 are either O or N; and
at least one of the side-chain substituents R at positions 3 and 6 contains a carboxyl group.

11. The method of claim 9 wherein the structure is formed from amino acids selected from the group consisting of glutamic acid, aspartic acid, lysine, ornithine and diaminopropionic acid cyclized by blocking free $\beta$-amino groups, heating in hot phenol under nitrogen at a temperature equivalent to 175° C., and removing the blocking groups.

12. The method of claim 11 further comprising succinylating a side chain of the diketopiperazine having a free amino group.

13. The method of claim 9 wherein the structure is selected from the group consisting of 2,5-diketo-3,6-di(aminobutyl)piperazine and 2,5-diketo-3,6-di(4-succinylaminobutyl)piperazine.

14. A method for administering a biologically active agent to a patient comprising providing the agent selected from the group consisting of proteins, peptides, polysaccharides, lipids, lipopolysaccharides, nucleic acids and other biologically active organic molecules, imaging agents, and cell specific targeting agents, in combination with microparticles formed of diketopiperazines, wherein the microparticles are stable at a first defined pH due to association and precipitation of the diketopiperazines and unstable at a second defined pH due to dissociation of the diketopiperazines.

15. The method of claim 14 wherein the agent is selected from the group consisting of hormones, anticoagulants, immunomodulating agents, cytotoxic agents, antibiotics, antivirals, antisense, antigens, and antibodies.

16. The method of claim 14 wherein the microparticles are further encapsulated within an enteric coating.

17. The method of claim 14 wherein the microparticles are stable at acidic pH and unstable at neutral or basic pH.

18. The method of claim 14 wherein the microparticles are unstable at acidic pH and stable at neutral or basic pH.

19. The method of claim 14 wherein the biological agent is insulin.

20. The method of claim 14 wherein the biological agent is heparin.

* * * * *